(12) United States Patent
Charles et al.

(10) Patent No.: US 11,382,501 B2
(45) Date of Patent: Jul. 12, 2022

(54) FOOT PEDAL CONTROLLED OCT-DISPLAY FOR VITREORETINAL SURGERY

(71) Applicant: Alcon Inc., Fribourg (CH)

(72) Inventors: Steven T. Charles, Germantown, TN (US); Tammo Heeren, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 523 days.

(21) Appl. No.: 16/168,382

(22) Filed: Oct. 23, 2018

(65) Prior Publication Data

US 2019/0125182 A1 May 2, 2019

Related U.S. Application Data

(60) Provisional application No. 62/577,773, filed on Oct. 27, 2017.

(51) Int. Cl.
*A61B 3/10* (2006.01)
*A61F 9/007* (2006.01)
(Continued)

(52) U.S. Cl.
CPC ............ *A61B 3/102* (2013.01); *A61B 3/0033* (2013.01); *A61B 3/0041* (2013.01);
(Continued)

(58) Field of Classification Search
CPC ..... A61B 3/0041; A61B 3/102; A61B 3/0025; A61B 3/0033; A61B 5/0066; A61B 3/0091; A61B 3/028; A61B 3/085; A61B 3/113; A61B 3/117; A61B 3/18; A61B 5/0073; A61B 3/13; A61B 2090/3735; A61B 3/1225; A61B 2017/00203; A61B 2017/00207; A61B 2017/00216; A61B 2017/00973; A61B 2034/2065; A61B 2090/372; A61B 3/005; A61B 3/0058; A61B 3/0075; A61B 3/1005; A61B 3/12; A61B 3/132; A61B 3/145; A61B 90/20; A61B 90/37; A61F 2009/00851; A61F 9/00736; A61F 2009/00872; A61F 2/16; A61F 9/007; A61F 9/00781; A61F 9/00825; A61F 9/0084
See application file for complete search history.

(56) References Cited

U.S. PATENT DOCUMENTS

| | | | |
|---|---|---|---|
| 2003/0137436 A1* | 7/2003 | Foong ..................... | G06F 3/021 341/21 |
| 2014/0218740 A1 | 8/2014 | Nebosis et al. | |
| 2017/0135574 A1* | 5/2017 | Charles .................. | A61B 3/145 |

FOREIGN PATENT DOCUMENTS

| | | |
|---|---|---|
| DE | 202014100609 U1 | 4/2014 |
| WO | 2017/139724 A1 | 8/2017 |

OTHER PUBLICATIONS

Carrasco-Zevallos et. al. "Review of intraoperative optical coherence tomography: technology and applications [Invited]." Biomedical Optics Express. Mar. 2017. vol. 8, No. 3. pp. 1607-1637.

(Continued)

*Primary Examiner* — Brandi N Thomas

(57) ABSTRACT

OCT-display for vitreoretinal surgery may be foot pedal controlled. Specifically, the tissue layers displayed in an en face image generated from OCT scanning may be navigated downward or upward based on user input supplied by a foot pedal device.

6 Claims, 3 Drawing Sheets

(51) Int. Cl.

| | |
|---|---|
| *A61B 3/00* | (2006.01) |
| *A61F 2/16* | (2006.01) |
| *H01H 21/26* | (2006.01) |
| *A61F 9/008* | (2006.01) |
| *A61B 90/00* | (2016.01) |
| *A61B 3/13* | (2006.01) |
| *A61B 3/14* | (2006.01) |
| *A61B 17/00* | (2006.01) |

(52) U.S. Cl.
CPC .............. *A61B 3/0075* (2013.01); *A61F 2/16* (2013.01); *A61F 9/007* (2013.01); *A61F 9/00736* (2013.01); *A61B 3/005* (2013.01); *A61B 3/0058* (2013.01); *A61B 3/1005* (2013.01); *A61B 3/13* (2013.01); *A61B 3/145* (2013.01); *A61B 2017/00973* (2013.01); *A61B 2090/3735* (2016.02); *A61F 2009/00851* (2013.01); *H01H 21/26* (2013.01)

(56) References Cited

OTHER PUBLICATIONS

Kang et al. "Real-time three-dimensional Fourier-domain optical coherence tomography video image guided microsurgeries." Journal of Biomedical Optics. Aug. 2012. vol. 17, No. 8. Article No. 081403.

\* cited by examiner

400 — METHOD FOR FOOT PEDAL CONTROLLED OCT-DISPLAY DURING VITREORETINAL SURGERY

402 DURING VIEWING OF AN INTERIOR PORTION OF AN EYE OF A PATIENT USING AN OPHTHALMIC VISUALIZATION SYSTEM, RECEIVE A FIRST INDICATION FROM A USER OF THE OPHTHALMIC VISUALIZATION SYSTEM OF A LOCATION IN THE EYE

404 BASED ON THE FIRST INSTRUCTION, PERFORM OCT SCANNING OF THE FIRST LOCATION, THE OCT SCANNING ENABLED TO OBTAIN AN EN FACE IMAGE OF TISSUE LAYERS AT THE LOCATION

406 CAUSE THE EN FACE IMAGE TO BE DISPLAYED TO THE USER, THE EN FACE IMAGE COMPRISING TISSUE LAYER DATA FOR EACH OF A PLURALITY OF TISSUE LAYERS OF THE EYE AT THE FIRST LOCATION

408 WHILE THE EN FACE IMAGE IS DISPLAYED TO THE USER, RECEIVE A SECOND INSTRUCTION FROM THE USER VIA A FOOT PEDAL DEVICE, WHERE THE SECOND INSTRUCTION INCLUDES ONE OF: A DOWNWARD INSTRUCTION TO DISPLAY A NEXT TISSUE LAYER FROM THE PLURALITY OF TISSUE LAYERS, AND AN UPWARD INSTRUCTION TO DISPLAY A PREVIOUS TISSUE LAYER FROM THE PLURALITY OF TISSUE LAYERS

410 BASED ON THE SECOND INSTRUCTION, DISPLAY THE TISSUE LAYER DATA FOR ONE OF THE NEXT TISSUE LAYER AND THE PREVIOUS TISSUE LAYER TO THE USER

FIG. 4

FOOT PEDAL CONTROLLED OCT-DISPLAY FOR VITREORETINAL SURGERY

FIELD

The present disclosure relates to ophthalmic surgery, and more specifically, to foot pedal controlled OCT-display for vitreoretinal surgery.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

Prior to or during vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus for vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. During a procedure, the field of view of the fundus may be presented to and viewed by the ophthalmologist using an ophthalmic visualization system which may include a microscope-based or microscope-less optical system such as NGENUITY® (Alcon Laboratories, Inc.).

In addition to optics for viewing the fundus, surgical microscopes may be equipped with optical coherence tomography (OCT) scanners to provide additional information about portions of eye tissue involved with the vitreoretinal surgery. The OCT scanner may enable imaging below a visible surface of the eye tissue to assist with vitreoretinal surgery. However, when performing vitreoretinal surgery, a hand- or voice-actuated command to control the display of OCT images may not be desirable or practical.

SUMMARY

In one aspect, a disclosed method supports performance of ophthalmic surgery with a foot pedal controlled OCT-display. During viewing of an interior portion of an eye of a patient using an ophthalmic visualization system, the method may include receiving a first instruction from a user of the ophthalmic visualization system of a location in the eye. Based on the first instruction, the method may include performing optical coherence tomography (OCT) scanning of the first location, the OCT scanning enabled to obtain a en face image of tissue layers at the location, and causing the en face image to be displayed to the user, the en face image comprising tissue layer data for each of a plurality of tissue layers of the eye at the first location. While the en face image is displayed to the user, the method may further include receiving a second instruction from the user via a foot pedal device. In the method, the second instruction may include one of: a downward instruction to display a next tissue layer from the plurality of tissue layers, and an upward instruction to display a previous tissue layer from the plurality of tissue layers. Based on the second instruction, the method may further include displaying the tissue layer data for one of the next tissue layer and the previous tissue layer to the user.

In any of the disclosed embodiments of the method, the second instruction may further include one of: a fast downward instruction to successively display a plurality of next tissue layers, and a fast upward instruction to successively display a plurality of previous tissue layers.

In any of the disclosed embodiments of the method, the second instruction may further specify a delay between successively displayed layers.

In any of the disclosed embodiments of the method, the downward instruction and the upward instruction may result from a first pressure applied to the foot pedal device. In the method, the fast downward instruction and the fast upward instruction may result from a second pressure applied to the foot pedal device, the second pressure being greater than the first pressure.

In any of the disclosed embodiments of the method, the second instruction may be received from the foot pedal device in response to actuating the foot pedal device using one of: a downward pressure actuation by the forefoot of the user, and an upward pressure actuation by the hind foot of the user.

Additional disclosed implementations include an OCT scanning controller, a surgical microscope, an ophthalmic visualization system, and an image processing system.

BRIEF DESCRIPTION OF THE DRAWINGS

For a more complete understanding of the present disclosure, reference is now made to the following description, taken in conjunction with the accompanying drawings, in which:

FIG. 4 is a flow chart of selected elements of a method for foot pedal controlled OCT-display for vitreoretinal surgery.

DETAILED DESCRIPTION

Figure 1:
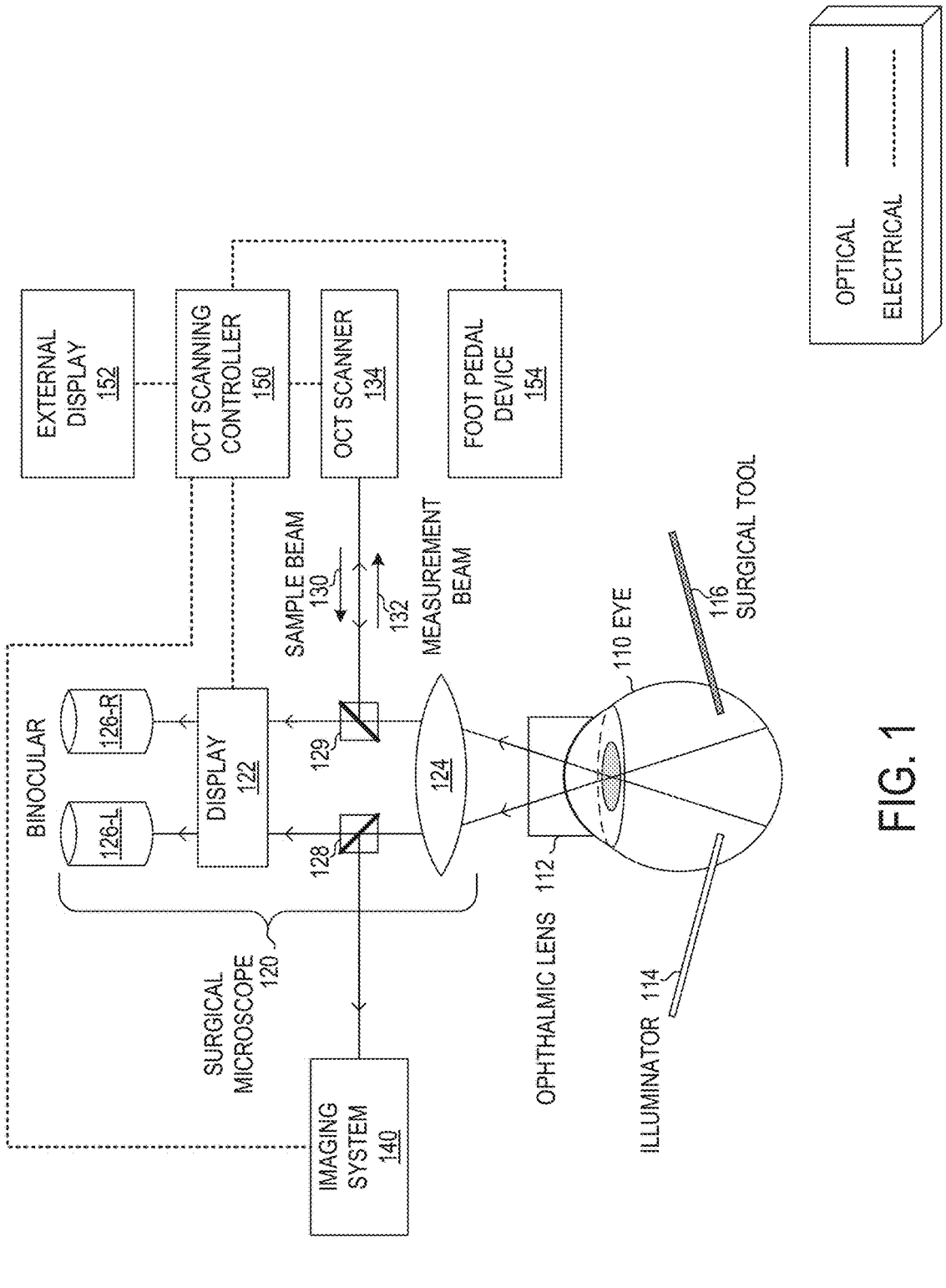
FIG. 1 is a block diagram of selected elements of an implementation of a surgical microscopy scanning instrument.

In the following description, details are set forth by way of example to facilitate discussion of the disclosed subject matter. It should be apparent to a person of ordinary skill in the field, however, that the disclosed implementations are exemplary and not exhaustive of all possible implementations.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

The present disclosure relates to foot pedal controlled OCT-display for vitreoretinal surgery. Specifically, during vitreoretinal surgery, the surgeon is typically engaged with full attention and is using both hands to operate using surgical microscope. Furthermore, when OCT scanning is performed, the surgeon may view a display of an OCT image in the surgical field of view of the surgical microscope. When the OCT image is an en face image, the surgeon may desire to view individual tissue layers from the en face image, for example, corresponding to tissue layers involved with surgical operations that the surgeon is performing. Using image processing, the individual tissue layers may be resolved and segmented from the OCT image. However, the ability of the surgeon to provide user input or to operate controls for selecting the display of the tissue layer in the en face image may be limited. A hand-operated selection control of the tissue layer (such as panel mounted controls, touch screen, etc.) may be unsuitable or impossible for the surgeon to operate while performing surgery. A voice-operated selection control of the tissue layer may also be unsuitable due to concerns about reliability, language customization, and a slow speed of voice recognition. Therefore, voice-operated controls may be particularly suitable for selecting options involving a single command, rather than for continuously selecting the tissue layer in the en face image, which may involve rapid and repetitive user input.

As will be described in further detail, foot pedal controlled OCT-display for vitreoretinal surgery may enable selection of the tissue layer in an en face image generated by OCT scanning and displayed during vitreoretinal surgery. The foot pedal controlled OCT-display during vitreoretinal surgery disclosed herein may involve the use of a foot pedal with varying pressure sensitivity for selective user input. The foot pedal controlled OCT-display during vitreoretinal surgery disclosed herein may enable the user (the surgeon) to control the display of the tissue layer in the en face image using the fore foot or the hind foot to directionally navigate through the tissue layers. In this manner, the foot pedal controlled OCT-display during vitreoretinal surgery disclosed herein may provide a foot-operated control of the tissue layer display that is reliable, fast, universal, and unambiguous, thereby providing greater ease of use, which is desirable.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110, and for foot pedal controlled OCT-display during vitreoretinal surgery, as disclosed herein. As shown, instrument 100 includes a surgical microscope 120, an OCT scanning controller 150, an external display 152, an OCT scanner 134, and a foot pedal device 154. Also shown in FIG. 1 are an imaging system 140, an ophthalmic lens 112, as well as a surgical tool 116 and an illuminator 114.

As shown, an example surgical microscope 120 is depicted in schematic form to illustrate optical functionality. It will be understood that embodiments of surgical microscope 120 may include various other electronic and mechanical components, in different implementations. It is noted that, in various embodiments, instrument 100 may include any suitable ophthalmic visualization system in addition to or in lieu of surgical microscope 120, including a microscope-free visualization platform such as NGENUITY®. Accordingly, while the particular optical design discussed with reference to FIG. 1 is specific to an ophthalmic visualization system that comprises microscope 120, one skilled in the art will appreciate that alternative optical arrangements to support other ophthalmic visualization systems are within the scope of the disclosure.

In the example shown in FIG. 1, objective 124 may represent a selectable objective to provide a desired magnification or field of view of the fundus. Objective 124 may receive light from the fundus of eye 110 via ophthalmic lens 112 that rests on a cornea of eye 110. It is noted that various types of ophthalmic lenses 112 may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may be split at beam splitter 128, from where imaging system 140 and left ocular 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right ocular 126-R. Display 122 may represent an optoelectronic component, such as an image processing system that receives the data from OCT scanning controller 150 and generates image output for left ocular 126-L and right ocular 126-R, respectively. In some implementations, display 122 includes miniature display devices that output images to binoculars 126 for viewing by the user. It is noted that the optical arrangement depicted in FIG. 1 is exemplary and may be implemented differently in other implementations. For example, the left and right beams may be reversed or combined in different implementations.

As described above, the optical system in surgical microscope 120 using binoculars 126 may provide a certain degree of depth visualization or 3-dimensional (3-D) display capability. Although integration of OCT with surgical microscope 120 is shown in FIG. 1 using an analog optical system, it will be understood that another ophthalmic visualization system may be used to implement surgical microscope 120 in various implementations. For example, instead of integrating display 122 within binoculars 126, the ophthalmic visualization system used with instrument 100 may be implemented digitally without binoculars 126 and by using an image sensor for each of the left beam and the right beam, such as a video camera. The left and right images from the respective image sensors may be used to generate a 3-D capable display that is viewed on a corresponding monitor, such as external display 152, rather than using binoculars 126, which may be omitted in a digital implementation of the ophthalmic visualization system. In certain implementations, surgical microscope 120 as depicted in FIG. 1 may be accordingly implemented using NGENUITY® 3D Visualization System (Alcon Laboratories, Inc.), which provides a platform for digitally assisted vitreoretinal surgery (DAVS).

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between imaging system 140 and OCT scanning controller 150 may support digital image data, OCT scanning controller 150 may perform image processing in real-time with relatively high frame refresh rates, such that a user of surgical microscope 120 may experience substantially instantaneous feedback to user input for controlling the selected portion of eye 110 for scanning, as well as other operations, as disclosed herein. External display 152 may output similar images as display 122, but may represent a stand-alone monitor for viewing by various personnel during vitreoretinal surgery. Display 122 or external display 152 may be implemented as a liquid crystal display screen, a computer monitor, a television, a tablet, a touchscreen, a 3-D visualization system, a projector, viewing glasses or goggles, or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. In certain embodiments, imaging system 140 may receive a portion of the right light beam, or both the left and right light beam, to enable imaging system 140 to independently process, display, store, and otherwise manipulate light beams and image data, and support 3-D visualization. Accordingly, imaging system 140 may represent any of a variety of different kinds of imaging systems, as desired.

As shown, OCT scanner 134 may represent an implementation of various kinds of OCT scanners. It is noted that other types of optical scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. OCT scanning controller 150 may interface with OCT scanner 134, for example, to send commands to OCT scanner 134 indicating the selected location to generate scan data, and to receive the scan data from OCT scanner 134. It is noted that OCT scanner 134 may represent various types of OCT instruments and configurations, as desired, such as but not limited to time domain OCT (TD-OCT) and frequency domain OCT (FD-OCT), such as spectral-domain OCT (SD-OCT) and swept-source OCT (SS-OCT). In particular, the scan data generated by OCT scanner 134 may include two-dimensional (2D) scan data of a line scan (B-scan) and three-dimensional (3D) scan data for an area scan (C-scan). The scan data may represent a depth profile of the scanned tissue that enables imaging below a visible surface within the fundus of eye 110.

In FIG. 1, foot pedal device 154 may represent any of a variety of footswitches or other devices for foot pedal actuation (see also FIG. 3), including but not limited to footswitch controllers like used with the Centurion® Vision System manufactured by Alcon®. In particular, foot pedal device 154 may provide for one of a forward actuation and a reverse actuation and may be enabled for detection of an applied foot pressure to foot pedal device 154.

In operation of instrument 100, the user may view the fundus of eye 110 using binoculars 126 or external display 152 while vitreoretinal surgery is performed on eye 110. In other embodiments of instrument 100, the user may view the fundus of eye 110 using microscope-free visualization platform such as NGENUITY®. The user may provide user input in the form of a first indication to OCT scanning controller 150 to initiate an OCT scan. It is noted that a user input, indication, confirmation, or selection received by instrument 100 may be communicated using a keyboard, mouse, touch-screen, voice command, gesture, eye tracking, or other user interface coupled to scanning controller 150, foot pedal controller 154, imaging system 140, or other components of instrument 100. The first indication may specify a location of the OCT scan in a surgical field of surgical microscope 120 where the user intends to view an OCT image, such as an en face image. OCT scanning controller 150 may, in turn, communicate with OCT scanner 134 to control scanning operations and perform a real-time OCT scan to generate first scan data at the location. The OCT scanning may be performed continuously or at a high frequency, such that the result of the OCT scan in the form of an OCT image appears to be continuously generated and updated. The OCT image may be displayed to the user using display 122, for example, to display the OCT image in the surgical field visible using binoculars 126. In some implementations, the OCT image may also or alternatively be displayed using external display 152 or a visualization platform such as NGENUITY®. In various implementations, the OCT image may be an en face image.

Either prior to or subsequent to display of the OCT image, the user may activate functionality for foot pedal controlled OCT-display during vitreoretinal surgery. For example, the user may select a corresponding feature provided as a menu option by OCT scanning controller 150 to activate functionality for foot pedal controlled OCT-display during vitreoretinal surgery. The user may then provide a second indication in the form of user input to OCT scanning controller 150 using foot pedal device 154, when the user desires to control the OCT-display.

For example, when the OCT image is an en face image, OCT scanning controller 150 may be enabled to perform image processing to segment the OCT image data into specific tissue layers. Because the tissue layers may not be perfectly flat, the image processing may detect the individual tissue interfaces, such as from the B-scan, and may identify the tissue layers in the en face image. When the en face image is displayed to the user, such as within the surgical field of view using surgical microscope 120 during vitreoretinal surgery, foot pedal device 154 may be used to control the OCT-display of the en face image. Specifically, foot pedal device 154 may be enabled to detect a downward pressure from either the forefoot or the hind foot of the user (see also FIG. 3). A first pressure detected from the forefoot of the user may generate a downward instruction for OCT scanning controller 150, while the first pressure detected from the hind foot of the user may generate an upward instruction for OCT scanning controller 150. When the downward instruction is received from foot pedal device 154, OCT scanning controller 150 may then display a next deeper tissue layer in the en face image (if possible), for example, by removing all tissue layers above the next deeper tissue layer in the OCT-display of the en face image. Conversely, when the upward instruction is received from foot pedal device 154, OCT scanning controller 150 may then display a previous tissue layer in the en face image (if possible), for example, by removing all tissue layers above the previous tissue layer in the OCT-display of the en face image. It will be understood that when the OCT-display is at the bottom most tissue layer in the OCT image data, the downward instruction may have no effect on the OCT-display, and that when the OCT-display is at the top most tissue layer in the OCT image data, the upward instruction may have no effect on the OCT-display.

Furthermore, foot pedal device 154 may be enabled to detect and respond to various degrees of foot pressure sensitivity used as user input. For example, a second pressure detected from the forefoot of the user may generate a fast downward instruction for OCT scanning controller 150, when the second pressure is greater than the first pressure. Similarly, the second pressure detected from the hind foot of the user may generate a fast upward instruction for OCT scanning controller 150. Any suitable technique may be used by OCT scanning controller 150 to determine whether the speed of a detected downward or upward instruction is sufficient to trigger the fast instruction response discussed herein. For example, OCT scanning controller 150 may determine whether a detected pressure constitutes a fast downward or updward instruction by, for example, comparing a detected rate of change of a current detected pressure to a predetermined rate-of-change threshold stored in a memory, or by comparing the detected rate-of-change of a current detected pressure with the rate of change of previously detected pressure inputs. When a fast downward instruction is received from foot pedal device 154, OCT scanning controller 150 may then begin to display successively deeper tissue layers in the en face image (if possible). Conversely, when the fast upward instruction is received from foot pedal device 154, OCT scanning controller 150 may begin to display successively previous tissue layers in the en face image (if possible). The display of the successive tissue layers may be performed using a delay in between the display of individual tissue layers, such as a user-selectable delay. When the second pressure is released from foot pedal device 154, the display of the successive tissue layers may freeze at a currently displayed tissue layer. In this manner, the user may control the display of the en face image during vitreoretinal surgery without the use of hands or voice commands, which may be practical and reliable and desirable.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some implementations.

Figure 2:
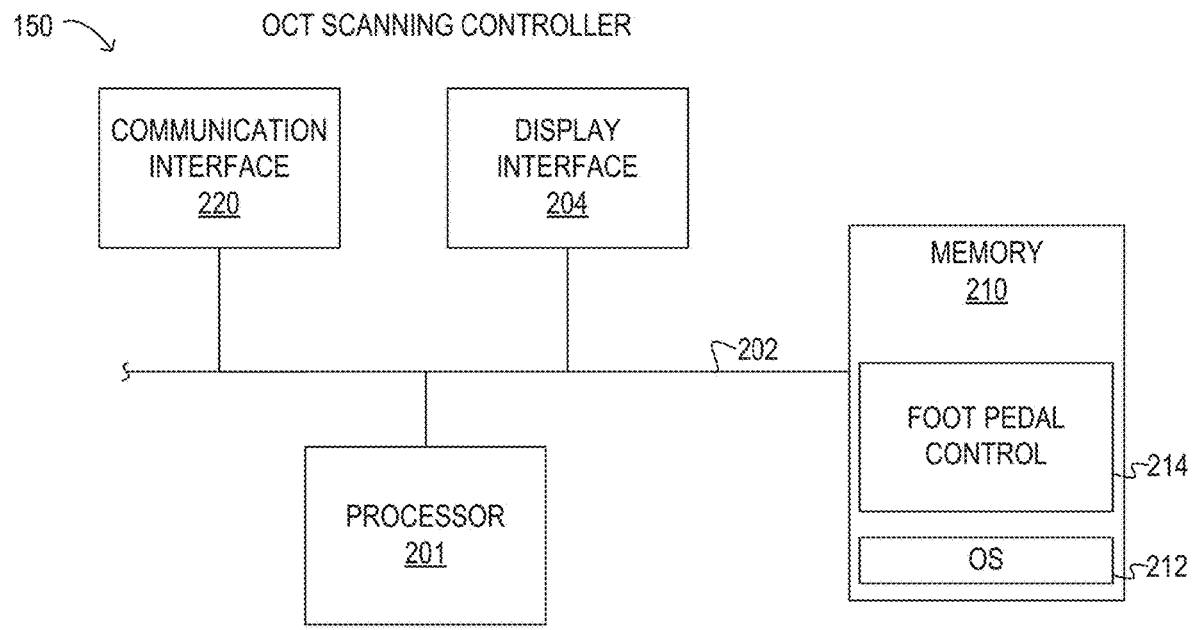
FIG. 2 is a block diagram of selected elements of an implementation of a scanning controller.

Referring now to FIG. 2, a block diagram illustrating selected elements of an implementation of OCT scanning controller 150, described above with respect to FIG. 1, is presented. In the implementation depicted in FIG. 2, OCT scanning controller 150 includes processor 201 coupled via shared bus 202 to memory media collectively identified as memory 210.

OCT scanning controller 150, as depicted in FIG. 2, further includes communication interface 220 that can interface OCT scanning controller 150 to various external entities, such as OCT scanner 134 or imaging system 140, among other devices. In some implementations, communication interface 220 is operable to enable OCT scanning controller 150 to connect to a network (not shown in FIG. 2). In implementations suitable for foot pedal controlled OCT-display during vitreoretinal surgery, OCT scanning controller 150, as depicted in FIG. 2, includes display interface 204 that connects shared bus 202, or another bus, with an output port for one or more displays, such as display 122 or external display 152.

In FIG. 2, memory 210 encompasses persistent and volatile media, fixed and removable media, and magnetic and semiconductor media. Memory 210 is operable to store instructions, data, or both. Memory 210 as shown includes sets or sequences of instructions, namely, an operating system 212, and a foot pedal control application 214. Operating system 212 may be a UNIX or UNIX-like operating system, a Windows® family operating system, or another suitable operating system. Foot pedal control application 214 may enable OCT scanning controller 150 to perform operations for foot pedal controlled OCT-display during vitreoretinal surgery, as disclosed herein.

Figure 3:
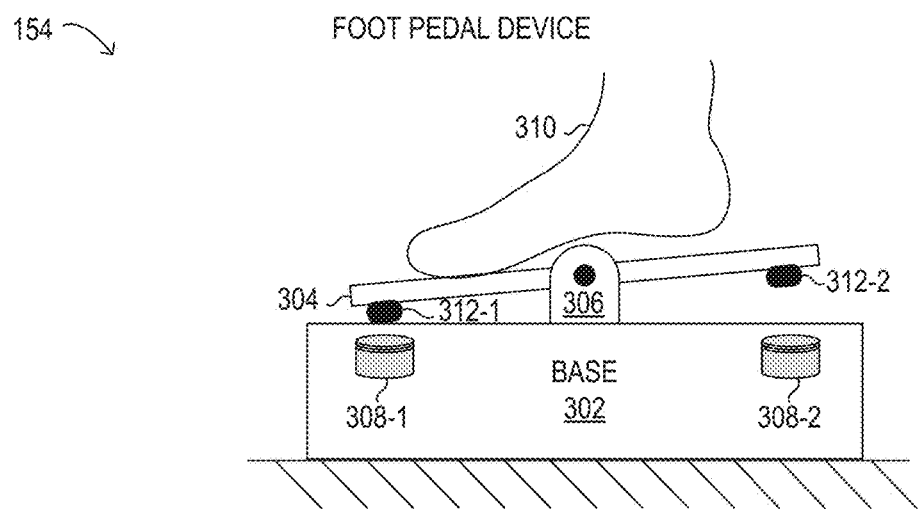
FIG. 3 is a depiction of a surgical field of view using a surgical microscopy scanning instrument.

Referring now to FIG. 3, a depiction of an example foot pedal device 154 is illustrated. FIG. 3 is a schematic illustration and is not drawn to scale or perspective. In FIG. 3, foot pedal device 154 is shown resting on a surface, such as the floor or the ground, during operation. A foot 310 represents the foot of the user operating foot pedal device 154. Foot pedal device 154 is shown comprising a base 302, a hinge 306 on which a foot pedal 304 is mounted and enabled to partially rotate, as well as two load cells 308. Additionally, foot pedal device 154 may have an electronic interface (not shown) for communicating with a controller, such as OCT scanning controller 150, for example. The electronic interface of foot pedal device 154 may be a wired or a wireless interface, in different implementations.

In operation, foot pedal device 154 includes foot pedal 304, which may partially rotate in multiple directions. In some implementations, foot pedal 304 may be spring loaded, such that foot pedal 304 returns to a start position when foot 310 is removed, such as a level or neutral start position. Foot pedal 304 is further equipped with a forward stop 312-1 and a reverse stop 312-2, shown as pads mounted on a back face of foot pedal 304. It will be understood that various different geometries and arrangements for stops 312 may be used in different implementations. Stops 312 are arranged to apply force to corresponding load cells 308. Specifically, forward stop 312-1 may apply force to a forward load cell 308-1, while reverse stop 312-2 may apply force to a reverse load cell 308-2. The degree or value of the force applied may be determined by the force applied by foot 310, as desired by the user. Then, using the fore foot of foot 310 to apply pressure by pressing down on a front portion of foot pedal 304, forward load cell 308-1 may detect a force, while reverse load cell 308-2 detects zero load or force. Conversely, using the hind foot of foot 310 to apply pressure by pressing down on a rear portion of foot pedal 304, reverse load cell 308-2 may detect a force, while forward load cell 308-1 detects zero load or force. In this manner, a forward or reverse directional control may be applied by foot 310.

Additionally, because load cells 308 can detect a value of the force, or can measure the force, a threshold value of force may be used to signify a secondary command. For example, when the force value is less than the threshold value, a first command may be indicated, and when the force value is greater than the threshold value, a second command may be indicated.

Although operation of foot pedal device 154 with load cells is illustrated, it will be understood that other types of sensors, such a rotary encoder at hinge 306 to detect a degree of rotation of foot pedal 304, may be used in different implementations.

In operation for foot pedal controlled OCT-display during vitreoretinal surgery, when an en face image generated from OCT scanning is displayed to the user, foot pedal device 154 may be used to control the tissue layer display of the en face image. By using image processing on the en face image (or the OCT scan data used to represent the en face image), the individual tissue layers may be detected and segmented, even when the tissue layers vary in thickness or orientation. As a result, the display of the en face image may be segmented by tissue layer, while foot pedal device 154 is used to select the tissue layer. Specifically, a first pressure may be applied to forward load cell 308-1 by foot 310, as described above, to indicate a downward instruction for navigating the tissue layers in the en face image. When the first pressure is applied to reverse load cell 308-2, an upward instruction for navigating the tissue layers may be indicated. The downward and upward instructions may result in exactly one tissue layer being advanced in the downward or upward direction from the en face image. It will be understood that an upward instruction at the top tissue layer in the en face image may have no effect, and similarly, a downward instruction at the bottom tissue layer in the enface image may also have no effect.

Furthermore, when a second pressure is applied to load cells 308, a fast instruction may be generated that indicates continuous navigation in a desired direction through the tissue layers in the en face image. The continuous navigation through the tissue layers in the en face image may include a delay at each successive tissue layer. The second pressure may be greater than the first pressure, and may be distinguished from the first pressure using a pressure threshold that is greater than the first pressure. In some implementations, the pressure threshold may be selectable by the user. Specifically, the pressure may be applied to forward load cell 308-1 by foot 310, as described above, to indicate a fast downward instruction for navigating the tissue layers in the en face image by successively displaying a plurality of next tissue layers (e.g., tissue layers progressively closer to the back of the eye). When the second pressure is applied to reverse load cell 308-2, an upward instruction for navigating the tissue layers may indicate successively displaying a plurality of previous tissue layers (e.g., tissue layers progressively closer to the front of the eye). It will understood that various other types of instructions and indications may be used with foot pedal device 154, such as foot taps, double foot taps, and different degrees of force.

Referring now to FIG. 4, a flow chart of selected elements of an implementation of a method 400 for foot pedal controlled OCT-display during vitreoretinal surgery, as described herein, is depicted in flowchart form. Method 400 describes steps and procedures that may be performed while surgical microscopy scanning instrument 100 is operated to view the fundus of an eye and perform surgical procedures based on the view of the fundus. Accordingly, at least certain portions of method 400 may be performed by foot pedal control application 214. It is noted that certain operations described in method 400 may be optional or may be rearranged in different implementations. Method 400 may be performed by foot pedal application 214 to interact with a surgeon or other medical personnel, referred to herein as a "user".

Prior to method 400, it may be assumed that surgical microscopy scanning instrument 100 is being used to view an interior portion of an eye of a patient, such as described in FIG. 1. Then, method 400 may begin, at step 402, by receiving a first indication from a user of an ophthalmic visualization system of a location in the eye. Based on the first instruction, at step 404, OCT scanning of the first location is performed, the OCT scanning enabled to obtain an en face image of tissue layers at the location. At step 406, the en face image is caused to be displayed to the user, the en face image comprising tissue layer data for each of a plurality of tissue layers of the eye at the first location. While the en face image is displayed to the user, at step 408, a second instruction is received from the user via a foot pedal device, where the second instruction includes one of: a downward instruction to display a next tissue layer (e.g., closer to the back of the eye) from the plurality of tissue layers, and an upward instruction to display a previous tissue layer (e.g., closer to the front of the eye) from the plurality of tissue layers. Based on the second instruction, at step 410, the tissue layer data is displayed for one of the next tissue layer and the previous tissue layer to the user.

As disclosed herein, OCT-display during vitreoretinal surgery may be foot pedal controlled. Specifically, the tissue layers displayed in an en face image generated from OCT scanning may be navigated downward or upward based on user input supplied by a foot pedal device.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method, comprising:
   during viewing of an interior portion of an eye of a patient using an ophthalmic visualization system, receiving a first instruction from a user of the ophthalmic visualization system of a location in the eye;
   based on the first instruction, performing optical coherence tomography (OCT) scanning of the first location, the OCT scanning enabled to obtain a plurality of en face images of a corresponding plurality of tissue layers at the location;
   causing a first en face image to be displayed to the user, the first en face image comprising tissue layer data for one of the plurality of tissue layers of the eye at the first location;
   while the first en face image is displayed to the user, receiving a second instruction from the user via a foot pedal device, wherein the second instruction includes one of: a downward instruction to display a next tissue layer from the plurality of tissue layers, and an upward instruction to display a previous tissue layer from the plurality of tissue layers; and based on the second instruction, displaying the tissue layer data for one of the next tissue layer and the previous tissue layer to the user, wherein the plurality of en face images is displayed consecutively in the same order as the tissue layers are ordered in the eye.

2. The method of claim 1, wherein the second instruction further comprises one of:

a fast downward instruction to successively display a plurality of next tissue layers; and a fast upward instruction to successively display a plurality of previous tissue layers.

3. The method of claim 2, wherein the second instruction further specifies a delay between successively displayed layers.

4. The method of claim 2, wherein the downward instruction and the upward instruction result from a first pressure applied to the foot pedal device, and wherein the fast downward instruction and the fast upward instruction result from a second pressure applied to the foot pedal device, the second pressure being greater than the first pressure.

5. The method of claim 1, wherein the second instruction is received from the foot pedal device in response to actuating the foot pedal device using one of: a downward pressure actuation by the forefoot of the user, and an upward pressure actuation by the hind foot of the user.

6. The method of claim 1 wherein the location in the eye is a retina of the eye and the en face images are ordered according to the layers of the retina.

\* \* \* \* \*